US009717929B2

(12) United States Patent
Chopra et al.

(10) Patent No.: US 9,717,929 B2
(45) Date of Patent: Aug. 1, 2017

(54) DENTIFRICE COMPOSITIONS CONTAINING CALCIUM SILICATE AND A BASIC AMINO ACID

(75) Inventors: Suman Chopra, Monroe, NJ (US); Rahul Patel, Parsippany, NJ (US); Lynette Anne Zaidel, Cranford, NJ (US)

(73) Assignee: Colgate-Palmolive Company, New York, NY (US)

( * ) Notice: Subject to any disclaimer, the term of this patent is extended or adjusted under 35 U.S.C. 154(b) by 1276 days.

(21) Appl. No.: 12/961,706

(22) Filed: Dec. 7, 2010

(65) Prior Publication Data

US 2012/0141588 A1 Jun. 7, 2012

(51) Int. Cl.

| | |
|---|---|
| ***A61K 9/14*** | (2006.01) |
| ***A61K 8/44*** | (2006.01) |
| ***A61Q 11/00*** | (2006.01) |
| ***A61P 25/00*** | (2006.01) |
| ***A61P 43/00*** | (2006.01) |
| ***A61P 31/04*** | (2006.01) |
| ***A61P 29/00*** | (2006.01) |
| ***A61K 8/02*** | (2006.01) |
| ***A61K 8/25*** | (2006.01) |

(52) U.S. Cl.

CPC ............ *A61Q 11/00* (2013.01); *A61K 8/0241* (2013.01); *A61K 8/25* (2013.01); *A61K 8/44* (2013.01); *A61K 2800/412* (2013.01)

(58) Field of Classification Search

USPC ........................................................... 424/49

See application file for complete search history.

(56) References Cited

U.S. PATENT DOCUMENTS

| | | | | |
|---|---|---|---|---|
| 3,535,421 | A | 10/1970 | Briner et al. | |
| 3,538,230 | A | 11/1970 | Pader et al. | |
| 3,678,154 | A | 7/1972 | Widder et al. | |
| 3,696,191 | A | 10/1972 | Weeks | |
| 3,862,307 | A | 1/1975 | Di Giulio | |
| 3,937,807 | A | 2/1976 | Haefele | |
| 3,959,458 | A | 5/1976 | Agricola et al. | |
| 3,991,177 | A | 11/1976 | Vidra et al. | |
| 4,051,234 | A | 9/1977 | Gieske et al. | |
| 4,058,595 | A | 11/1977 | Colodney | |
| 4,154,815 | A | 5/1979 | Pader | |
| 4,340,583 | A | 7/1982 | Wason | |
| 4,355,022 | A | 10/1982 | Rabussay | |
| 4,842,847 | A | 6/1989 | Amjad | |
| 4,866,161 | A | 9/1989 | Sikes et al. | |
| 4,885,155 | A | 12/1989 | Parran, Jr. et al. | |
| 4,992,420 | A | 2/1991 | Neeser | |
| 5,000,939 | A | 3/1991 | Dring et al. | |
| 5,004,597 | A | 4/1991 | Majeti et al. | |
| 5,762,911 | A * | 6/1998 | Kleinberg et al. | 424/49 |
| 6,524,558 | B2 | 2/2003 | Kleinberg et al. | |
| 2002/0037258 | A1 | 3/2002 | Dodd et al. | |
| 2007/0059257 | A1 | 3/2007 | Estrada et al. | |
| 2008/0233054 | A1 | 9/2008 | Kleinberg et al. | |
| 2008/0268001 | A1 | 10/2008 | Zaidel et al. | |
| 2008/0305027 | A1 | 12/2008 | Johnston et al. | |
| 2009/0202451 | A1 | 8/2009 | Prencipe et al. | |

FOREIGN PATENT DOCUMENTS

| | | |
|---|---|---|
| CN | 1377252 | 10/2002 |
| CN | 101600443 | 12/2009 |
| JP | 2003506391 | 2/2003 |
| TW | 200934517 | 8/2009 |
| WO | WO0078270 | 12/2000 |
| WO | WO0110392 | 2/2001 |
| WO | WO2008068149 | 6/2008 |
| WO | 2009099452 A1 | 8/2009 |
| WO | WO2009100265 | 8/2009 |
| WO | WO2010090855 | 8/2010 |

OTHER PUBLICATIONS

Ono et al., "Development of Porous Silica Production by Hydrothermal Method". High Pressure Research 2001:20;307-310.*

Taddei et al., "Vibrational study on the bioactivity of Portland cement-based materials for endodontic use." Journal of Molecular Structure, vols. 924-926, Apr. 30, 2009, pp. 548-554.

Great Dictionary of Medical Terms., Fedotov V.D., Tsentrpoligraph, 2007, p. 340, right column.

Farid Ghazali et al: "Review Article—Permeability of Dentine", Review Article—Permeability of Dentine, vol. 10, No. 1, Jan. 1, 2003, pp. 27-36, XP0552232959.

* cited by examiner

*Primary Examiner* — Walter Webb

(57) ABSTRACT

An oral care composition includes an effective amount of a basic amino acid in free or salt form; and an effective amount of calcium silicate particles. The calcium silicate particles have an average diameter of less than about 5 microns, such that they can occlude dentinal tubules of the teeth. An oral care method includes applying the composition to an oral cavity of a subject to reduce or inhibit hypersensitivity of the teeth and to achieve other benefits.

1 Claim, No Drawings

DENTIFRICE COMPOSITIONS CONTAINING CALCIUM SILICATE AND A BASIC AMINO ACID

FIELD OF THE INVENTION

This invention relates to oral care compositions comprising dentin occluding particles together with a basic amino acid or salt thereof and to methods of making and using such compositions.

BACKGROUND OF THE INVENTION

Dentin is a portion of the tooth internal to the enamel and cementum that has a radially striated appearance owing to a large number of fine canals or tubules known as the dentinal tubules. Tubules run from the pulp cavity to the periphery of the dentin and are generally about two microns in diameter at their base and somewhat narrower at their periphery. Tubules are not usually exposed to the environment in the oral cavity, as they are usually covered by enamel or cementum. The cementum in turn is often covered by the gums.

It is commonly understood that partially or fully exposed tubules can lead to tooth sensitivity, an irritating and painful condition. In this theory, recession of the gum line exposes cementum to erosion. The eroded cementum in turn exposes the hollow dentinal tubules. The exposed tubules cause nerves within the tooth to be affected excessively by external oral stimuli because material and energy transfer between the exterior and interior of the tooth is accelerated through the tubules. Common environmental stimuli, such as heat, cold, chemicals and physical and mechanical pressure or stimuli, such as brushing, are able to irritate the nerve through the open dentin tubules and thereby create pain. The pain of sensitive teeth appears to result from these stimuli, which apparently cause fluid movements in the dentinal tubules that activate pulpal nerve endings.

Conventionally, two approaches have been taken to treat or ameliorate tooth sensitivity. Under one approach, the chemical environment proximal to the nerve is altered by application of various agents, such that the nerve is not stimulated, or not stimulated as greatly. Known agents useful in this chemical approach, including potassium salts (such as potassium nitrate, potassium bicarbonate, and potassium chloride), strontium salts, zinc salts, and chloride salts.

The second approach involves the mechanical shielding of the nerve by, e.g., blocking of the dentinal tubules wholly or partially with tubule blocking agents (i.e., occluding agents).

Despite the foregoing developments, it is desired to provide alternative methods and compositions for treating and preventing tooth hypersensitivity.

SUMMARY OF THE INVENTION

Accordingly, a first aspect of the invention is an oral care composition comprising:

an effective amount of a basic amino acid in free or salt form; and an effective amount of calcium silicate particles.

A second aspect of the invention is an oral care method comprising applying to an oral cavity of a subject the composition of the invention in an amount effective to: reduce or inhibit formation of dental caries; reduce, repair or inhibit pre-carious lesions of the enamel; reduce or inhibit demineralization and promote remineralization of the teeth; reduce hypersensitivity of the teeth; reduce or inhibit gingivitis; promote healing of sores or cuts in the mouth; reduce levels of acid producing bacteria; increase relative levels of arginolytic bacteria; inhibit microbial biofilm formation in the oral cavity; raise and/or maintain plaque pH at levels of at least pH 5.5 following sugar challenge; reduce plaque accumulation; treat, reduce, relieve or alleviate dry mouth; whiten teeth; reduce erosion; promote systemic health; immunize teeth against cariogenic bacteria; and/or clean teeth and the oral cavity.

In certain embodiments of the invention, the calcium silicate particles have an average diameter less than 5 microns.

In certain embodiments of the invention, the composition further comprises potassium nitrate. In certain of these embodiments, the potassium nitrate is present at a concentration of 1-10 wt % based on a weight of the composition.

In certain embodiments of the invention, the effective amount of the basic amino acid is 0.1-20 wt. % based on a weight of the composition.

In certain embodiments of the invention, the effective amount of calcium silicate particles is 5-20 wt. % based on a weight of the composition. The calcium silicate may have a pH between 8.4 and 11.2 in a 5% calcium silicate solution.

In certain embodiments of the invention, the basic amino acid is arginine.

In certain embodiments of the invention, the basic amino acid is partially or wholly in a salt form selected from the group consisting of arginine bicarbonate, arginine hydrochloride, arginine phosphate and combinations thereof.

In certain embodiments of the invention, the basic amino acid is arginine bicarbonate.

In certain embodiments of the invention, the average diameter of the calcium silicate particles is from 2 microns to 5 microns.

In certain embodiments of the invention, the composition further comprises precipitated calcium carbonate or silica.

In certain embodiments of the invention, the composition further comprises a soluble fluoride salt, an anionic surfactant and an antibacterial agent.

In certain embodiments of the invention, the composition is aqueous.

In certain embodiments of the invention, the composition is in the form of a toothpaste further comprising at least one ingredient selected from the group consisting of water, an abrasive, a surfactant, a foaming agent, a vitamin, a polymer, an enzyme, a humectant, a thickener, an antimicrobial agent, a preservative, a flavoring and a coloring.

In certain embodiments of the invention, the composition is applied to the oral cavity in an amount effective to reduce hypersensitivity of the teeth.

DETAILED DESCRIPTION

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients as is common in the art, notwithstanding that these ingredients may react with one another in the actual formulation as it is made, stored and used and such products are intended to be covered by the formulations described.

Unless otherwise specified, all percentages and amounts expressed herein and elsewhere in the specification should be understood to refer to percentages by weight. The amounts given are based on the active weight of the material.

Composition of the Invention

Amounts of ingredients will vary based on the nature of the delivery system and the particular ingredient. For example, the basic amino acid may be present at levels from. e.g. about 0.1 to about 20 wt. % (expressed as weight of free base), e.g., about 0.1 to about 3 wt. % for a mouthrinse, about 1 to about 10 wt. % for a consumer toothpaste or about 7 to about 20 wt. % for a professional or prescription treatment product. Fluoride may be present at levels of, e.g., about 25 to about 10,000 ppm, for example about 25 to about 250 ppm for a mouthrinse, about 750 to about 2,000 ppm for a consumer toothpaste, or about 2,000 to about 10,000 ppm for a professional or prescription treatment product. Levels of antibacterial will vary similarly with levels used in toothpaste being, e.g., about 5 to about 15 times greater than used in mouthrinse. For example, a triclosan mouthrinse may contain, e.g., about 0.03 wt. % triclosan while a triclosan toothpaste may contain about 0.3 wt. % triclosan.

Basic Amino Acids

The basic amino acids which can be used in the compositions and methods of the invention include not only naturally occurring basic amino acids, such as arginine, lysine, serine and histidine, but also any basic amino acids having a carboxyl group and an amino group in the molecule which are water-soluble and provide an aqueous solution with a pH of about 7 or greater.

Accordingly basic amino acids suitable for use in the invention include, but are not limited to, arginine, lysine citrulline, ornithine, creatine, histidine, diaminobutanoic acid, diaminoproprionic acid, salts thereof or combinations thereof. In certain embodiments, the basic amino acids are selected from arginine, citrulline and ornithine, with arginine being most preferred.

In certain embodiments, the basic amino acid comprises at least one intermediate produced in the arginine deiminase system. The intermediates produced in the arginine deiminase system may be useful in an oral care composition to provide plaque neutralization for caries control and/or prevention. Arginine is a natural basic amino acid that may be found in the oral cavity. Arginine in the mouth may be utilized by certain dental plaque bacterial strains such as *S. sanguis, S. gordonii, S. parasanguis, S. rattus, S. milleri, S. anginosus, S. faecalis, A. naeslundii, A. odonolyticus, L. cellobiosus, L. brevis, L. fermenium, P. gingivalis*, and *T. denticola* for their survival. Such organisms may perish in an acidic environment that may be present at areas close to the tooth surface where acidogenic and aciduric cariogenic strains may use sugars to produce organic acids. Thus, these arginolytic strains may break down arginine to ammonia to provide alkalinity to survive and, in addition, buffer the plaque and make a hostile environment for the cariogenic systems.

Such arginolytic organisms may catabolize arginine by an internal cellular enzyme pathway system called the "arginine deiminase system" whereby intermediates in the pathway are formed. In this pathway, L-arginine may be broken down to L-citrulline and ammonia by arginine deiminase. L-citrulline may then be broken down by ornithane trancarbamylase in the presence of inorganic phosphate to L-ornithine and carbamyl phosphate. Carbamate kinase may then break down carbamyl phosphate to form another molecule of ammonia and carbon dioxide and in the process also forms ATP (adenosine 5'-triphosphate). ATP may be used by the arginolytic bacteria as an energy source for growth. Accordingly, when utilized the arginine deiminase system may yield two molecules of ammonia.

It has been found that, in certain embodiments, the ammonia may help in neutralizing oral plaque pH to control and/or prevent dental caries.

The oral care composition of some embodiments of the present invention may include intermediates produced in the arginine deiminase system, such as citrulline, ornithine and/or carbamyl phosphate.

The oral care composition may include the above-described intermediates in an effective amount. In some embodiments the oral care composition includes about 1 mmol/L to about 10 mmol/L intermediate. In other embodiments, the oral care composition includes about 3 mmol/L to about 7 mmol/L intermediate. In other embodiments, the oral care composition includes about 5 mmol/L intermediate.

The compositions of the invention are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids, which form a physiological acceptable anion e.g. hydrochloride or bromide salt and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example by reacting a sufficiently basic compound such as an amine with a suitable acid affording a physiologically acceptable anion.

In certain embodiments, the basic amino acid is present in an amount of 0.5-20 wt. % or 5-15 wt. % or about 10 wt. % based on the total composition weight.

Calcium Silicate

In addition to the basic amino acid, compositions of the invention comprise calcium silicate. The calcium silicate is in the form of particles of a size such that they are effective to occlude dentinal tubules. Thus, the calcium silicate particles preferably have an average diameter of 0.5-10 microns or 1-9 microns or 2-5 microns, with an average diameter below 5 microns being most preferred. The calcium silicate preferably has a surface area of 20 to 400 m2/g and a pore volume of 0.01 to 1 cc/g.

Compositions of the invention comprise calcium silicate particles in an amount effective to occlude dentinal tubules. In certain embodiments of the inventive composition, the calcium silicate particles are present in an amount of 1-20 wt. % or 5-15 wt. % or about 10 wt. % based on the total weight of the composition.

Suitable calcium silicate particles can be obtained commercially, or prepared by known methods, such as the method disclosed in US 20080305027 A1. In certain embodiments, the calcium silicate has a high surface area. Although no phosphate pre-treatment is necessary, in certain embodiments, the calcium silicate is pre-treated with phosphate. High surface area calcium silicate would be greater than 20 m2/g.

Nerve Desensitizing Agent

Certain embodiments of the inventive composition include a chemical agent effective to treat or prevent tooth hypersensitivity, such as potassium salts (such as potassium nitrate, potassium bicarbonate, and potassium chloride), strontium salts, zinc salts, and chloride salts.

In certain embodiments, such agents constitute 0.01-10 wt. % or 1-8 wt. % of the composition.

Fluoride Ion Source

The oral care compositions may further include one or more fluoride ion sources e.g. soluble fluoride salts. A wide variety of fluoride ion-yielding materials can be employed as sources of soluble fluoride in the present compositions. Examples of suitable fluoride ion-yielding materials are found in U.S. Pat. No. 3,535,421, U.S. Pat. No. 4,885,155 and U.S. Pat. No. 3,678,154.

Representative fluoride ion sources include, but are not limited to, stannous fluoride, sodium fluoride, potassium fluoride, sodium monofluorophosphate. sodium fluorosilicate, ammonium fluorosilicate, amine fluoride, ammonium fluoride and combinations thereof. In certain embodiments the fluoride ion source includes stannous fluoride, sodium fluoride, sodium monofluorophosphate as well as mixtures thereof.

In certain embodiments, the oral care composition of the invention may also contain a source of fluoride ions or fluorine-providing ingredient in amounts sufficient to supply about 25-25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A mouthwash, for example would typically have about 100 to about 250 ppm fluoride. A toothpaste for general consumer use would typically have about 1000 to about 1500 ppm, with pediatric toothpaste having somewhat less. A dentifrice or coating for professional application could have as much as 5,000 or even 25,000 ppm fluoride.

Fluoride ion sources may be added to the compositions of the invention at a concentration of about 0.01 wt. % to about 10 wt. %, or about 0.03 wt. % to about 5 wt. %, or about 0.1 wt. % to about 1 wt. %, based on the weight of the composition. Weights of fluoride salts to provide the appropriate level of fluoride ion will obviously vary based on the weight of the counter ion in the salt.

Where the composition comprises calcium bicarbonate, sodium monofluorophosphate is preferred to sodium fluoride for stability reasons.

Abrasives

In addition to the calcium silicate, which is an abrasive that acts as an occluding agent, compositions of the invention can further comprise one or more additional abrasives, including but not limited to: precipitated calcium carbonate (PCC); a calcium phosphate abrasive (e.g. tricalcium phosphate ($Ca_3(PO_4)_2$). hydroxyapatite ($Ca_{10}(PO_4)_6(OH)_2$), dicalcium phosphate dihydrate ($CaHPO_4.2H_2O$, also sometimes referred to herein as DiCal) or calcium pyrophosphate; silica abrasives such as precipitated silicas having a mean particle size of up to about 20 μm (e.g., ZEODENT 115, marketed by J. M. Huber); sodium metaphosphate; potassium metaphosphate; aluminum silicate; calcined alumina; and bentonite or other siliceous materials.

The additional abrasives preferably have an average diameter of 0.1-30 microns, or 5-15 microns.

The silica abrasives can be from precipitated silica or silica gels, such as the silica xerogels described in U.S. Pat. No. 3,538,230 to Pader et al. and U.S. Pat. No. 3,862,307 to Digiulio. Particular silica xerogels are marketed under the trade name SYLOID by the W. R. Grace & Co. Davison Chemical Division. The precipitated silica materials include those marketed by the J. M. Huber Corp. under the trade name ZEODENT, including the silica abrasives carrying the designations ZEODENT 115 and ZEODENT 119. These silica abrasives are described in U.S. Pat. No. 4,340,583 to Wason.

In certain embodiments, abrasive materials useful in the practice of the oral care compositions in accordance with the invention include silica gels and precipitated amorphous silica having an oil absorption value of about less than 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of 3-12 μm, or 5-10 μm.

In certain embodiments, the abrasive materials comprise a large fraction of very small particles, e.g., having an average diameter less than about 5 μm. For example, the abrasive materials can comprise small particle silica (SPS) having a d50 of about 3 to about 4 μm, for example, SORBOSIL AC43 (Ineos). Such small particles can contribute to the efficacy of formulations targeted at reducing hypersensitivity. The small particle component may be present in combination with a second larger particle abrasive. In certain embodiments, for example, the formulation comprises about 5 to about 25 wt. % small particles e.g., SPS, and about 10 to about 30 wt. % of a conventional abrasive.

Low oil absorption silica abrasives particularly useful in the practice of the invention are marketed under the trade designation SYLODENT XWA by Davison Chemical Division of W.R. Grace & Co., Baltimore. Md. 21203. SYLODENT 650 XWA, a silica hydrogel composed of particles of colloidal silica having a water content of about 29 wt. % averaging about 7 to about 10 μm in diameter, and an oil absorption of less than about 70 cc/100 g of silica, is an example of a low oil absorption silica abrasive useful in the practice of the present invention. In certain embodiments, the abrasive is present in the oral care composition of the present invention at a concentration of 10-60 wt. %, 20-45 wt. % or 30-50 wt. %.

In certain embodiments, the basic amino acid is incorporated into a dentifrice composition having a base formulation comprising calcium carbonate, and in particular precipitated calcium carbonate, as an abrasive. L-arginine and arginine salts such as arginine bicarbonate are themselves distinctly bitter in taste, and in aqueous solution can also impart a fishy taste. The addition of L-arginine or arginine salts to a base dentifrice formulation comprising calcium carbonate can provide a significant enhancement of taste and mouthfeel attributes to the dentifrice formulation and to an increase in the overall acceptance of the product to a consumer.

Foaming Agents

The oral care compositions of the invention can optionally include an agent to increase the amount of foam that is produced when the oral cavity is brushed.

Illustrative examples of agents that increase the amount of foam include but are not limited to polyoxyethylene and certain polymers including but not limited to, alginate polymers.

The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for use in the invention will have a molecular weight of about 200,000 to about 7,000,000. In one embodiment the molecular weight will be about 600,000 to about 2,000,000 and in another embodiment about 800,000 to about 1,000,000. Suitable polyoxyethylenes include the POLYOX family of polyoxyethylenes from Dow Chemical Co.

The polyoxyethylene may be present in an amount of 1-90 wt. %., or 5-50 wt. % or 10-20 wt. % based on the weight of the composition. The dosage of foaming agent in the oral care composition (i.e., a single dose) is 0.01-0.9 wt. %, or 0.05-0.5 wt. %, or 0.1-0.2 wt. %.

Surfactants

Another agent optionally included in the oral care composition of the invention is a surfactant or a mixture of compatible surfactants. Suitable surfactants are those which are reasonably stable throughout a wide pH range, for example, anionic, cationic, nonionic or zwitterionic surfactants. Non-limiting examples of suitable surfactants are disclosed in U.S. Pat. No. 3,959,458 to Agricola et al., U.S. Pat. No. 3,937,807 to Haefele and U.S. Pat. No. 4,051,234 to Gieske et al.

In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. Mixtures of anionic surfactants may also be utilized.

In another embodiment, cationic surfactants useful in the present invention can be broadly defined as derivatives of aliphatic quaternary ammonium compounds having one long alkyl chain containing about 8 to about 18 carbon atoms, such as lauryl trimethylammonium chloride, cetyl pyridinium chloride, cetyl trimethylammonium bromide, di-isobutylphenoxyethyldimethylbenzylammonium chloride, coconut alkyltrimethyl-ammonium nitrite, cetyl pyridinium fluoride and mixtures thereof.

Illustrative cationic surfactants include the quaternary ammonium fluorides described in U.S. Pat. No. 3,535,421 to Briner et al. Certain cationic surfactants can also act as germicides in the compositions.

Illustrative nonionic surfactants that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to the PLURONICS (BASF Corp.), polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

In certain embodiments, zwitterionic synthetic surfactants useful in the present invention can be broadly described as derivatives of aliphatic quaternary ammonium, phosphonium and sulfonium compounds, in which the aliphatic radicals can be straight chain or branched, and wherein one of the aliphatic substituents contains about 8 to about 18 carbon atoms and one contains an anionic water-solubilizing group e.g., carboxy, sulfonate, sulfate, phosphate or phosphonate. Illustrative examples of the surfactants suited for inclusion in the composition include, but are not limited to, sodium alkyl sulfate, sodium lauroyl sarcosinate, cocoamidopropyl betaine and polysorbate 20, and combinations thereof.

In a particular embodiment, the composition of the invention comprises an anionic surfactant, e.g., sodium lauryl sulfate.

The surfactant or mixtures of compatible surfactants can be present in the compositions of the present invention in an amount of 0.1-5.0 wt. %, 0.3-3.0 wt. % or 0.5-2.0 wt. % based on a weight of the composition.

Flavoring Agents

The oral care compositions of the invention may also include a flavoring agent.

Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit and orange.

Also useful are such chemicals as menthol, carvone, and anethole. Certain embodiments employ the oils of peppermint and spearmint.

The flavoring agent is incorporated in certain embodiments of the composition at a concentration of 0.1-5 wt. % or 0.5-1.5 wt. % based on the weight of the composition. The dosage of flavoring agent in the individual oral care composition dosage (i.e., a single dose) is 0.001-0.05 wt. % or 0.005-0.015 wt. %.

Chelating Agents

The oral care compositions of the invention also may optionally include one or more chelating agents able to complex calcium found in the cell walls of the bacteria. Binding of this calcium weakens the bacterial cell wall and augments bacterial lysis.

A group of compounds suitable for use as chelating agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least about 1.0 wt. % pyrophosphate ions, e.g., 1.5-6 wt. % or 3.5-6 wt. % of such ions.

Polymers

The oral care compositions of the invention also optionally include one or more polymers such as polyethylene glycols, polyvinylmethyl ether maleic acid copolymers, and polysaccharides (e.g., cellulose derivatives, such as carboxymethyl cellulose or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts.

Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000.

These copolymers are available for example as GANTREZ AN 139 (M.W. 500,000), AN 119 (M.W. 250,000) and S-97 Pharmaceutical Grade (M.W. $2\times10^6$ Daltons) from ISP Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103 (M.W. 10,000) and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is an acid containing an olefinic double bond which readily functions in polymerization because of its presence in the monomer molecule either in the alpha-beta position with respect to a carboxyl group or as part of a terminal methylene grouping.

Illustrative of such acids are acrylic, methacrylic, ethacrylic, alpha-chloroacrylic, crotonic, beta-acryloxy propionic, sorbic, alpha-chlorsorbic, cinnamic, beta-styryl acrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide-2-methylpropane sulfonic acid having a molecular weight of about 1,000 to about 2,000,000, described in U.S. Pat. No. 4,842,847 to Zahid.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 to Sikes.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of 0.1-10.0 wt. % or 0.5-5.0 wt. % based on the composition weight are used.

Water

Water may also be present in the oral compositions of the invention. Water employed in the preparation of commercial oral compositions is preferably deionized and free of organic impurities. Water commonly makes up the balance of the compositions and constitutes about 5% to about 90%, about 20% to about 60% or about 10% to about 30% by weight of the oral compositions. This amount of water includes the free water which is added plus that amount which is introduced with other materials such as with sorbitol or any components of the invention.

Humectants

Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally constitutes 15-70 wt. % or 30-65 wt. % of the dentifrice composition.

Suitable humectants include edible polyhydric alcohols, such as glycerine, sorbitol, xylitol, propylene glycol, as well as other polyols and mixtures of these humectants. Mixtures of glycerin and sorbitol may be used in certain embodiments as the humectant component of the toothpaste compositions herein.

In addition to the above-described components, the embodiments of this invention can contain a variety of optional dentifrice ingredients some of which are described below.

Optional ingredients include, for example, but are not limited to adhesives, sudsing agents, flavoring agents, sweetening agents, additional antiplaque agents, abrasives, and coloring agents. These and other optional components are further described in U.S. Pat. No. 5,004,597 to Majeti, U.S. Pat. No. 3,959,458 to Agricola et al. and U.S. Pat. No. 3,937,807 to Haefele.

Methods of Manufacture

The compositions of the present invention can be made using methods which are common in the oral product area.

In one illustrative embodiment, the oral care composition is made by neutralizing or partially neutralizing arginine in a gel phase with an acid, e.g., phosphoric acid, hydrochloric acid or carbonic acid, and mixing to form a first mixture. Actives such as, for example vitamins, CPC, fluoride, abrasives (including occlusive agent(s)), and any other desired active ingredients are added to first mixture and mixed to form second mixture. Where the final product is a toothpaste, a toothpaste base, for example, dicalcium phosphate precipitated calcium carbonate and/or silica, is added to second mixture and mixed. The final slurry is formed into an oral care product.

Composition Use

The present invention in its method aspect involves applying to the oral cavity a safe and effective amount of the compositions described herein.

The compositions and methods according to the invention are useful in a method to protect the teeth by facilitating repair and remineralization, in particular to reduce or inhibit formation of dental caries, reduce or inhibit demineralization and promote remineralization of the teeth, reduce hypersensitivity of the teeth as detected by hydraulic conductance, and reduce, repair or inhibit pre-carious lesions of the enamel, e.g., as detected by quantitative light-induced fluorescence (QLF) or electronic caries monitor (ECM).

QLF is a visible light fluorescence that can detect early lesions and longitudinally monitor the progression or regression. Normal teeth fluoresce in visible light. Demineralized teeth do not or do so only to a lesser degree. The area of demineralization can be quantified and its progress monitored. Blue laser light is used to make the teeth autofluoresce. Areas that have lost mineral have lower fluorescence and appear darker in comparison to a sound tooth surface. Software is used to quantify the fluorescence from a white spot or the area/volume associated with the lesion. Generally, subjects with existing white spot lesions are recruited as panelists. The measurements are performed in vivo with real teeth. The lesion area/volume is measured at the beginning of the clinical. The reduction (improvement)

in lesion area/volume is measured at the end of 6 months of product use. The data is often reported as a percent improvement versus baseline.

ECM is a technique used to measure mineral content of the tooth based on electrical resistance. Electrical conductance measurement exploits the fact that the fluid-filled tubules exposed upon demineralization and erosion of the enamel conduct electricity. As a tooth loses mineral, it becomes less resistive to electrical current due to increased porosity. An increase in the conductance of the patient's teeth therefore may indicate demineralization. Generally, studies are conducted on root surfaces with an existing lesion. The measurements are performed in vivo with real teeth. Changes in electrical resistance before and after 6 month treatments are made. In addition, a classical caries score for root surfaces is made using a tactile probe. The hardness is classified on a three point scale: hard, leathery or soft. In this type of study, typically the results are reported as electrical resistance (higher number is better) for the ECM measurements and an improvement in hardness of the lesion based on the tactile probe score.

The compositions of the invention are thus useful in a method to reduce pre-carious lesions of the enamel (as measured by QLF or ECM) relative to a composition lacking effective amounts of fluorine and/or arginine.

The compositions of the invention are additionally useful in methods to reduce harmful bacteria in the oral cavity, for example methods to reduce or inhibit gingivitis, reduce levels of acid producing bacteria, to increase relative levels of arginolytic bacteria, inhibit microbial biofilm formation in the oral cavity, raise and/or maintain plaque pH at levels of at least pH 5.5 following sugar challenge, reduce plaque accumulation and/or clean the teeth and oral cavity. Finally, by increasing the pH in the mouth and discouraging pathogenic bacteria, the compositions of the invention are useful to promote healing of sores or cuts in the mouth.

Enhancing oral health also provides benefits in systemic health, as the oral tissues can be gateways for systemic infections. Good oral health is associated with systemic health, including cardiovascular health. The compositions and methods of the invention provide particular benefits because basic amino acids, especially arginine, are sources of nitrogen which supply NO synthesis pathways and thus enhance microcirculation in the oral tissues. Providing a less acidic oral environment is also helpful in reducing gastric distress and creates an environment less favorable to *Helicobacter pylori*, which is associated with gastric ulcers. Arginine in particular is required for high expression of specific immune cell receptors, for example T-cell receptors, so that arginine can enhance an effective immune response. The compositions and methods of the invention are thus useful to enhance systemic health, including cardiovascular health.

The compositions and methods according to the invention can be incorporated into oral compositions for the care of the mouth and teeth such as toothpastes, transparent pastes, gels, mouth rinses, sprays and chewing gum.

EXAMPLES

The following examples further describe and demonstrate illustrative embodiments within the scope of the present invention. The examples are given solely for illustration and are not to be construed as limitations of this invention as many variations arc possible without departing from the spirit and scope thereof. Various modifications of the invention in addition to those shown and described herein should be apparent to those skilled in the art and are intended to fall within the appended claims.

Formulas containing calcium silicate showed better performance after acid challenge in comparison to control dentifrice without calcium silicate. Formulas containing calcium silicate were capable of nucleating crystals of hydroxyapatite when in solution with the ions commonly found in human saliva, such as phosphate. Hydroxyapatite formation from calcium silicate was comparable to that observed with bioactive glass. Dentinal occlusion experiments by confocal microscopy showed that toothpaste samples containing calcium silicate provide faster occlusion and the occlusion is acid resistant.

Example 1

Prototypes were prepared in a PCC and silica base with 13.86 wt. % arginine bicarbonate. Calcium silicate with average particle size less than 5 um was incorporated in the dentifrice. See Table 1 below for prototype formulations.

TABLE 1

| Ingredient | Formula I | Formula II | Formula III | Formula IV |
|---|---|---|---|---|
| Sorbitol | 23.0 | 23.0 | 20.0 | 20.0 |
| Vegetable Glycerin | 0 | 0 | 20.0 | 20.0 |
| Sodium CMC Type7 | 0.72 | 0.72 | 0.90 | 0.90 |
| Xhantan gum | 0.135 | 0.135 | 0 | 0 |
| Potassium Nitrate | 0 | 0 | 0 | 5.0 |
| Sodium Monofluorphosphate | 0.836 | 0.836 | 1.14 | 0.836 |
| Sodium Saccharin | 0.30 | 0.30 | 0.40 | 0.40 |
| Sodium Silicate | 0.80 | 0.80 | 0 | 0 |
| Titanium Dioxide | 0.50 | 0.50 | 0.75 | 0.75 |
| 75% Arginine Bicarbonate | 13.86 | 13.86 | 13.86 | 13.86 |
| Sodium Bicarbonate | 0.50 | 0.50 | 0 | 0 |
| Precipitated calcium carbonate | 35.0 | 25.0 | 0 | 0 |
| Synthetic amorphous silica (Zeo114) | 0 | 0 | 10.0 | 10.0 |
| Synthetic amorphous silica (Zeo165) | 0 | 0 | 2.0 | 2.0 |
| Calcium Silicate | 0.0 | 10.0 | 10.0 | 10.0 |
| Sodium lauryl sulfate | 1.40 | 1.40 | 1.50 | 1.50 |
| Flavor | 1.00 | 1.00 | 1.30 | 1.30 |
| Water (to balance) | QS | QS | QS | QS |

Hydroxyapatite Formation

A calcium silicate sample with a particle size less than 5 microns was immersed in a jar with PBS containing calcium and phosphate for seven days with continuous stirring. After seven days, the solution was filtered and solids were measured using a Perkin-Elmer FTIR. A spectra measured for the calcium silicate sample (A) and a control sample (Calcium Silicate in DI-Water) (B) subjected to the same conditions as the calcium silicate sample shows peaks at 561 $cm^{-1}$ and 601 $cm^{-1}$ that are indicative of the formation of hydroxyapatite by the calcium silicate sample. Based on previous experiments, it was determined that hydroxyapatite formation from calcium silicate is comparable to that observed with bioactive glass after seven days.

Example 2

In vitro testing of the hydraulic conductance of several different compositions was conducted. The results are shown below. Human dentin segments were cut from extracted molars, cleared of pulpal tissue and mounted on acrylic blocks, etched and connected to a Flodec apparatus to measure fluid flow rate (hydraulic conductance) through dentin. The first treatment was applied using a parafilm covered fingertip and was massaged for 1 minute. Treatments 2 and 3 were applied using a soft toothbrush for 1 minute. Following each of the 3 treatments, samples were rinsed with de-ionized (DI) water, connected to the Flodec apparatus, and the conductance was measured. Blocks were rinsed again and incubated in phosphate buffered saline (PBS) for at least 2 hours before the next treatment. Conductance was measured (70 cm water pressure) and reported as a % conductance relative to the etched baseline for each segment. After all treatments and measurements, the segments were incubated in PBS overnight, after which conductance was re-measured. The segments were challenged for one minute with 6% citric acid and conductance was measured again. Significantly higher reductions in dentin permeability were seen in Table 2 with Formula III vs. both a conventional silica dentifrice as well as a marketed dentifrice for hypersensitivity relief containing strontium acetate.

TABLE 2

| % Dentinal Fluid Flow vs. etched control | | | | | |
|---|---|---|---|---|---|
| Formula | Finger Application | Treatment 1 | Treatment 2 | Overnight | 6% Citric Acid Challenge |
| Formula III | 53.34 (0.45) | 38.58 (4.60) | 35.53 (7.66) | 36.97 (5.14) | 41.84 (6.84) |
| Strontium acetate anti-hypersensitity dentifrice | 89.98 (6.16) | 73.36 (13.81) | 55.66 (10.47) | 59.91 (10.82) | 80.58 (13.44) |
| Conventional silica dentifrice | — | 69.74 (10.56) | 73.18 (5.92) | 68.26 (8.99) | 81.81 (13.87) |
| Arginine/PCC | 50.28 (7.90) | 29.23 (10.88) | 28.40 (7.93) | 29.58 (11.00) | 40.26 (14.71) |

Properties of three calcium silicates with varying d50, d10 and d90 levels is shown in Table 3. Particle size distributions are commonly measured by a laser diffraction spectrometer and described using d10, d50 and d90 values. The d50 value is the median particles size meaning that 50% of the particle population is equal to or smaller than the d50 value. Similarly, 10% of the particle population is equal to or smaller than the d10 value in diameter and 90% of the particle population is equal to or smaller than the d90 value in diameter. Another way to express the particle size distribution is by cumulative volume percentage at or below at selected particle diameter. (CVP). The metric that best describes both the particle size distribution and the impact of particle size on the product in accordance with this invention is a CVP at or below 3.95 microns (CVP3.95). Calcium silicate 3 would found to be efficacious vs. non-efficacious calcium silicates.

TABLE 3

| Calcium Silicate | Efficacious | d50 | d10 | d90 | CVP3.95 |
|---|---|---|---|---|---|
| 1 | No | 8.23 | 1.45 | 19.37 | 27.88 |
| 2 | No | 5.85 | 3.07 | 10.53 | 21.78 |
| 3 | Yes | 3.27 | 1.72 | 6.9 | 64.42 |

Thus, the composition of the invention both occludes dentinal tubules and shows bioactivity as evidenced by the formation of hydroxyapatite. In addition, calcium silicate particles used in aqueous dentifrices of the invention will provide a reactive surface to nucleate calcium and phosphate ions in saliva.

What is claimed is:

1. An oral care composition for reducing hypersensitivity of the tooth comprising:□a. an effective amount of a basic amino acid in free or salt form; and □b. an effective amount of calcium silicate particles, wherein the calcium silicate particles have an average diameter of less than 5 microns, wherein the particles have a d50 of 2 μm to 5 μm, and a d90 of 5 μm to 10 μm, and a cumulative volume percentage at 3.95 of at least 50%.

* * * * *